United States Patent

Wiesendanger

[11] Patent Number: 5,961,498
[45] Date of Patent: Oct. 5, 1999

[54] CATHETER WITH TWO-PLY ADHESIVE LAYER

[75] Inventor: Hans Wiesendanger, Eschenz, Switzerland

[73] Assignee: Schneider (Europe) GmbH, Bulach, Switzerland

[21] Appl. No.: 08/992,939

[22] Filed: Dec. 17, 1997

[30] Foreign Application Priority Data

Aug. 29, 1997 [EP] European Pat. Off. ............ 97202661

[51] Int. Cl.⁶ ................................................. A61M 5/00
[52] U.S. Cl. .......................... 604/264; 156/158; 156/310
[58] Field of Search ................................... 604/264, 280, 604/96, 93, 103, 104, 282, 524, 525, 907; 606/108, 194; 156/158, 294, 310

[56] References Cited

U.S. PATENT DOCUMENTS

| | | | |
|---|---|---|---|
| 4,157,932 | 6/1979 | Hirata | 156/310 |
| 4,171,416 | 10/1979 | Motegi et al. | 526/245 |
| 4,769,099 | 9/1988 | Therriault et al. | . |
| 4,776,849 | 10/1988 | Shinno et al. | 604/283 |
| 4,863,449 | 9/1989 | Therriault et al. | . |
| 4,940,179 | 7/1990 | Soni | . |
| 5,147,315 | 9/1992 | Weber | . |
| 5,221,270 | 6/1993 | Parker | 604/282 |
| 5,234,416 | 8/1993 | Macaulay et al. | 604/282 |
| 5,279,560 | 1/1994 | Morrill et al. | 604/96 |
| 5,527,281 | 6/1996 | Haas | . |
| 5,545,151 | 8/1996 | O'Connor et al. | 604/282 |
| 5,643,209 | 7/1997 | Fugoso et al. | 604/96 |
| 5,653,691 | 8/1997 | Rupp et al. | . |
| 5,728,088 | 3/1998 | Magruder et al. | 604/892.1 |
| 5,733,400 | 3/1998 | Gore et al. | 156/158 |
| 5,749,852 | 5/1998 | Schwab et al. | 604/96 |
| 5,792,814 | 8/1998 | Oishi et al. | 525/119 |

FOREIGN PATENT DOCUMENTS

| | | |
|---|---|---|
| 0298634A1 | 1/1989 | European Pat. Off. . |
| 0456342A1 | 11/1991 | European Pat. Off. . |
| 0803264A1 | 10/1997 | European Pat. Off. . |

*Primary Examiner*—Wynn Wood Coggins
*Assistant Examiner*—LoAn H. Thanh
*Attorney, Agent, or Firm*—Crompton, Seager & Tufte, LLC

[57] ABSTRACT

A catheter with a first component, a second component, and a glue line disposed between the components which is filled with an adhesive layer joining the components. The adhesive layer is formed in two plies, whereby a first adhesive ply is bonded to the first component and a second adhesive ply is bonded to the first adhesive ply and to the second component. Thus, even catheter components which could not be bonded to each other with the use of a single-ply adhesive layer or could only be bonded with inadequate stability can be firmly bonded to each other. Moreover, one of the adhesive plies may be applied in the unassembled state of the components.

14 Claims, 2 Drawing Sheets

CATHETER WITH TWO-PLY ADHESIVE LAYER

BACKGROUND OF THE INVENTION

This application claims priority under 35 U.S.C. § 119 of European Patent Application No. 97202661.1, filed in the European Patent Office on Aug. 29, 1997, which is incorporated herein by reference in its entirety for all purposes.

The invention relates to a catheter with a first component, a second component, and a glue line, which is filled with an adhesive layer joining the components, disposed between the components.

In the manufacture of catheters for medical interventions, such as balloon or guide catheters for a percutaneous transluminal angioplasty or placement instruments for implantation of an endoprosthesis, many different materials are used. Primarily plastics are used, such as polyamide, polyimide, polyether ether ketone for catheter shafts, polycarbonate for connectors, nylon or polyethylene terephthalate for dilation balloons and polyurethane for catheter tips, but so are metal materials, such as nickel-titanium alloys for stiffer shaft sections, gold for x-ray impermeable marking rings or stainless steel for stiffening wires. Depending on the physical properties necessary for the function, a suitable material must be selected for each catheter component such that a fully assembled catheter has connection points with extremely varied pairs of materials to be joined. In practical use, some of the connections are exposed to intense mechanical loads and must meet the high safety standard of medical catheter technology. Compared to the attachment of shrink sleeves and welding, the gluing of catheter components is a relatively simple and, consequently, a popular joining technique.

With the large selection of available adhesives, most connections between the components of a catheter can be made quickly and with adequate stability. The adhesion of two catheter components now depends on whether an adhesive is available which, when solidified, forms in addition to the internal cohesive force, forms adhesive forces with the gluing surfaces of the two components to be connected as well. Due to the variety of component materials in terms of their chemical structure, which enables the formation of the adhesive forces, or in terms of their wettability, it happens that no adhesive material bonds adequately solidly with both catheter components at the same time. On the other hand, it is possible that with an adhesive which would bond with both components the hardening process cannot be performed because of structural constraints or would take too much time. For catheter technology, this means a limitation of the selection of materials or the use of connection techniques more expensive than gluing.

SUMMARY OF THE INVENTION

The object of the invention is a catheter whereby the aforementioned restrictions and disadvantages are overcome. In particular, components of a catheter should be solidly connected to each other even if their materials are difficult to glue as described above but a gluing technique must nevertheless be used.

If the adhesive layer is formed in two plies, whereby a first adhesive ply is joined to the first component and a second adhesive ply is joined to the first adhesive ply and to the second catheter component, catheter components which would either not be joinable at all or only with inadequate stability with a single-ply adhesive layer, can be firmly glued to each other. Moreover, it may be advantageous to apply a first adhesive ply in an unassembled state of the first component and to form the bond with a second component by means of a second adhesive ply in the final assembled state.

In a preferred embodiment of the invention, the adhesive plies are formed from chemically reacting adhesives since, for production of the bond, no high pressure is necessary, but rather as a rule, the attachment of the glued surfaces of the components to be connected is adequate. In addition, there is a large selection of chemically reactive adhesives even with different reaction mechanisms.

In advantageous forms of the invention, the adhesives have different reaction mechanisms since the firm connections between catheter components with highly different adhesion characteristics can be made. Preferably, one of the adhesives reacts through addition of moisture whereas the other adhesive reacts through the addition of energy. Thus, for example, a first adhesive ply which hardens through the addition of heat or light radiation may be applied on a first radiation resistant component in the unassembled state, without thereby damaging the other component, and the connection to the second component of the catheter can be made with the second component of the catheter by means of a second ply of adhesive hardened by moisture on the surface of the components to be joined with high stability in the final assembled state.

In an advantageous embodiment of the invention, the adhesive reacting through the addition of moisture is a cyanoacrylate and the adhesive reacting through the addition of energy hardens through radiation with ultraviolet light. Both adhesives are quick hardening and enable correspondingly short production times for a catheter according to the invention.

SUMMARY

In, the present invention relates to a catheter with a first component, a second component, and a glue line disposed between the components which is filled with an adhesive layer joining the components, wherein the adhesive layer is formed in two plies, whereby a first adhesive ply is bonded to the first component and a second adhesive ply is bonded to the first adhesive ply and to the second component. The adhesive plies may be formed by chemically reacting adhesives with differing reaction mechanisms. One adhesive may react through the addition of moisture whereas the other may react through the application of energy. A suitable adhesive which reacts through the addition of moisture is a cyanoacrylate. The adhesive which reacts through the application of energy can be hardened by radiation with ultraviolet light.

BRIEF DESCRIPTION OF THE DRAWINGS

Additional advantages are revealed through a preferred embodiment which is explained in detail with reference to the drawings, in which.

DETAILED DESCRIPTION OF THE INVENTION

Figure 1:
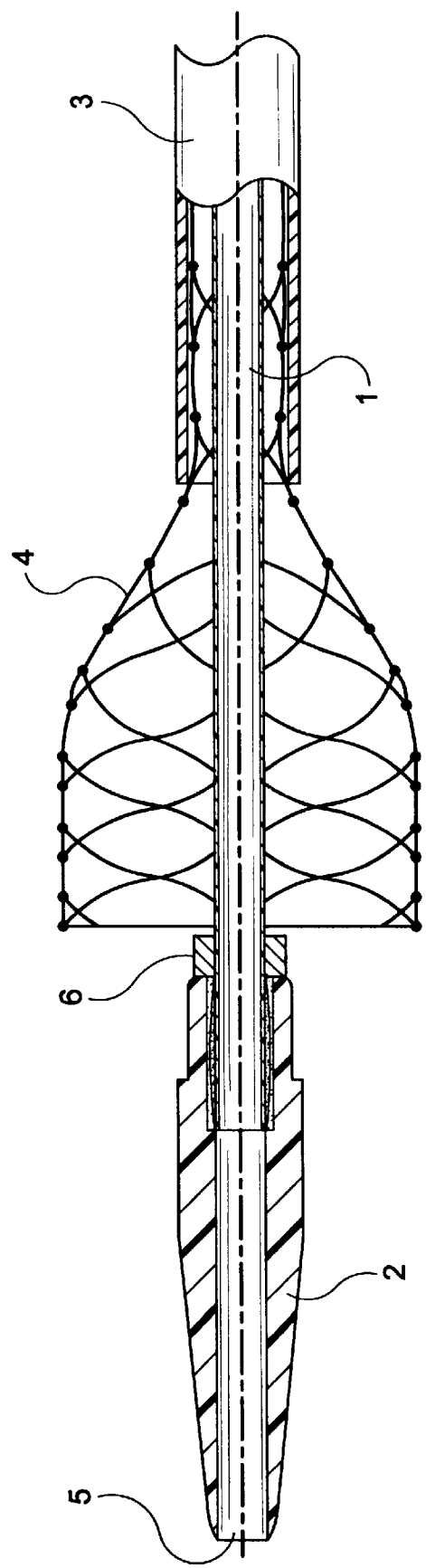
FIG. 1 depicts the distal section of a stent placement arrangement according to the invention in a partial cutaway.

FIG. 1 depicts a known stent placement arrangement using a self-expanding vascular support, also called a stent, which is introduced through a puncture opening in the blood vessel system, pushed to its implantation point, and finally released there. The stent expands through its own elasticity and presses from the inside against the vascular wall to be supported.

The stent placement arrangement has according to FIG. 1 an internal shaft 1 with a tip 2 and an external shaft 3, which are disposed inside one another and can be shifted relative to each other in the axial direction. The stent 4 is radially compressed for introduction and loaded between the internal shaft 1 and the external shaft 3, whereby the external shaft 3 is pushed from the proximal end to the tip 2 and forms a smooth, atraumatic transition therewith. The hollow tip 2 forms, with the likewise hollow internal shaft 1, a guidewire lumen 5 which runs the entire length of the catheter to accommodate a guidewire (not shown) With the tapering tip 2 in the front, the arrangement is pushed on the preplaced guidewire up to the implantation site, whereby the position of the arrangement in the vascular system may be made fluoroscopically visible using an x-ray impermeable marking ring 6. By retracting the external shaft 3 relative to the internal shaft 1, the self-expanding stent 4 is released, as shown.

During all these manipulations and in particular during the retraction of the catheter through narrow and injured vessels, all components connections, in particular that are between the internal shaft 1 and the tip 2, must have adequate stability, to prevent, for example, the danger of their loss inside the human body. Whereas the tip 2 is preferably made of a relatively soft polyurethane and has, generally, good adhesion characteristics, the internal shaft 1 is made of a stiffer substance, such as polyether ether ketone, which because of its poor wettability is only slightly adhesive. With a UV-hardening adhesive, it would be possible to obtain adequate stability of the connection; however, such an adhesive cannot be used here since the tip 2 is not permeable to ultraviolet light because of its x-ray impermeable additive.

Figure 2:
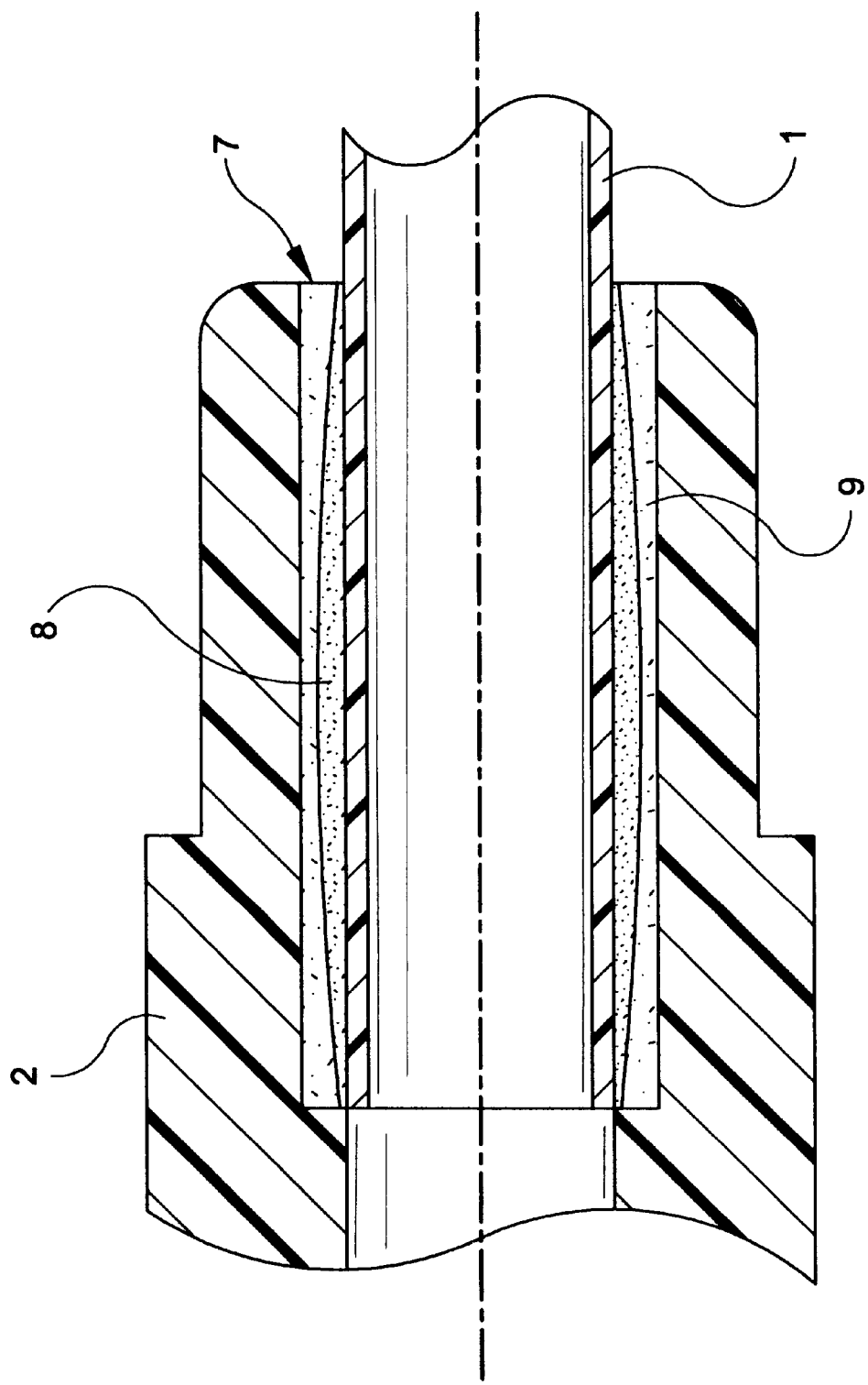
FIG. 2 depicts a connection point between components of the arrangement of FIG. 1 in longitudinal section.

According to FIG. 2, the glue line between the internal shaft and the tip 2 is filled by a two-ply adhesive layer 7, whereby the first adhesive ply 8 is connected with the internal shaft 1 and the second adhesive ply 9 is connected with the tip 2. The first adhesive ply 8 consists of a UV-hardening adhesive which is applied to the internal shaft 1 and hardened in the unassembled state, since the adhesive is then still accessible for radiation with ultraviolet light. Then, as a second adhesive ply, a cyanoacrylate is applied to the first adhesive ply and/or on the gluing surface of the tip 2, which in the assembled state is hardened by the surface moisture on the entire gluing surface. Through the two-ply adhesive layer 7, it is possible to increase the stability of the bond compared to a single-ply cyanoacrylate layer many times over.

The above-described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A catheter with a first component formed of a first material and a second component formed of a second material, wherein the first material has different adhesion characteristics than the second material, with a portion of a surface of each component aligned to form a space disposed between the components which is filled with an adhesive layer joining the components, wherein the adhesive layer is formed in two plies, whereby a first adhesive ply is bonded to the first component and a second adhesive ply is bonded to the first adhesive ply and to the second component, wherein said first ply has different adhesion characteristics than said second ply to form a more stable bond between the first and second materials than would otherwise be formed with only one adhesive ply.

2. The catheter of claim 1 wherein the adhesive plies are formed by chemically reacting adhesives.

3. The catheter of claim 2 wherein the adhesive plies are formed by chemically reacting adhesives with different reaction mechanisms.

4. The catheter of claim 3 wherein one adhesive reacts through the addition of moisture whereas the other reacts through the application of energy.

5. The catheter of claim 4 wherein the adhesive which reacts through the addition of moisture is a cyanoacrylate.

6. The catheter of claim 4 wherein the adhesive which reacts through the application of energy is hardened by radiation with ultraviolet light.

7. A catheter having a first component with a first surface defined thereon and a second component having a second surface defined thereon, the first component having different adhesion characteristics than the second component, said first and second surfaces aligned with a space therebetween filled with a first adhesive ply and a second adhesive ply, wherein the first ply has different adhesion characteristics than the second ply, wherein the first ply is more readily bondable to the second ply than the second surface.

8. The catheter of claim 7, wherein said first adhesive ply comprises an adhesive that is curable by light energy.

9. The catheter of claim 7, wherein said second adhesive ply comprises an adhesive that is curable by addition of moisture.

10. The catheter of claim 7, wherein said first adhesive ply is cured prior to assembly of said catheter.

11. The catheter of claim 7, wherein said second adhesive ply comprises a material which fails to form adequate adhesive force if bonded directly to the material of the first component.

12. A catheter having a first component with a first surface defined thereon and a second component having a second surface defined thereon, said first and second surfaces aligned with a space therebetween filled with a first adhesive ply which is cured by application of light energy and a second adhesive ply which is cured by addition of moisture.

13. The catheter of claim 12, wherein said second adhesive ply comprises a material which fails to form adequate adhesive force if bonded directly to the material of the first component.

14. The catheter of claim 12, wherein said first adhesive ply is at least partially cured prior to application of said second adhesive ply.

* * * * *